(12) United States Patent
Knapp et al.

(10) Patent No.: US 9,618,432 B2
(45) Date of Patent: Apr. 11, 2017

(54) PRESSURE REACTOR FOR TREATING A SAMPLE FLUID

(71) Applicant: Günter Knapp, Graz (AT)

(72) Inventors: Günter Knapp, Graz (AT); Helmar Wiltsche, Graz (AT)

(73) Assignee: Günter Knapp, Graz (AT)

( * ) Notice: Subject to any disclaimer, the term of this patent is extended or adjusted under 35 U.S.C. 154(b) by 781 days.

(21) Appl. No.: 14/011,345

(22) Filed: Aug. 27, 2013

(65) Prior Publication Data

US 2014/0065721 A1    Mar. 6, 2014

(30) Foreign Application Priority Data

Aug. 28, 2012   (AT) .................................. A 935/2012

(51) Int. Cl.
*G01N 1/18* (2006.01)
*G01N 1/44* (2006.01)
*G01N 1/28* (2006.01)

(52) U.S. Cl.
CPC .................. *G01N 1/44* (2013.01); *G01N 1/28* (2013.01); *Y10T 436/25375* (2015.01)

(58) Field of Classification Search
None
See application file for complete search history.

(56) References Cited

U.S. PATENT DOCUMENTS 5,672,316 A    9/1997   Knapp

FOREIGN PATENT DOCUMENTS

| DE | 1 745 266 | 8/1971 |
|---|---|---|
| DE | 195 06 577 | 9/1995 |
| GB | 1001587 | 8/1963 |

*Primary Examiner* — Robert Xu
(74) *Attorney, Agent, or Firm* — Henry M. Feiereisen LLC

(57) ABSTRACT

A pressure reactor for treating a sample fluid includes an oven, a sample line partly arranged in the oven, and a pressure line arranged in surrounding relation to the sample line and partly arranged in the oven. The sample line has an outlet opening into the pressure line. A contamination blocking apparatus is disposed in the pressure line for forming a contamination barrier which has at least one section arranged between the outlet opening and the oven and which delimits a contamination-free region in the pressure line. The outlet opening of the sample line is arranged in the contamination-free region of the pressure line.

11 Claims, 1 Drawing Sheet

PRESSURE REACTOR FOR TREATING A SAMPLE FLUID

CROSS-REFERENCES TO RELATED APPLICATIONS

This application claims the priority of Austrian Patent Application, Serial No. AT 935/2012, filed Aug. 28, 2012, pursuant to 35 U.S.C. 119(a)-(d), the disclosure of which is incorporated herein by reference in its entirety as if fully set forth herein.

BACKGROUND OF THE INVENTION

The present invention relates to a pressure reactor for treating a sample fluid

The following discussion of related art is provided to assist the reader in understanding the advantages of the invention, and is not to be construed as an admission that this related art is prior art to this invention.

A pressure reactor can be used for carrying out wet-chemical processes especially on a laboratory scale, e.g. for the breakdown of organic samples for trace element analysis. In this case, a sample fluid is guided in a sample line through an oven, wherein a chemical reaction of the individual components of the sample fluid occurs within the sample line. In order to increase the boiling point and therefore the achievable reaction temperatures, the sample line can be arranged in a pressure vessel. In this case, a free end of the sample line can be arranged in the pressure vessel, thus leading to a pressure balance between the sample line and a pressure vessel. As a result of this pressure balance, the mechanical properties of sample line will not limit the maximum achievable pressure, thus enabling substantially higher pressures.

Conventional pressure reactors have shortcomings because at high temperature components of the sample fluid, especially various acids, diffuse in the region of the oven through the sample line into the surrounding pressure line and accumulate there. These diffusing components can then condensate in the pressure vessel to cause contamination of the emerging finished sample fluid and to distortion of the result of the analysis.

It would therefore be desirable and advantageous to provide an improved pressure reactor which obviates prior art shortcomings and is structured to prevent contamination of a sample fluid.

SUMMARY OF THE INVENTION

According to one aspect of the present invention, a pressure reactor for treating a sample fluid includes an oven, a sample line partly arranged in the oven, a pressure line arranged in surrounding relation to the sample line and partly arranged in the oven, with the sample line having an outlet opening into the pressure line, and a contamination blocking apparatus disposed in the pressure line for forming a contamination barrier which has at least one section arranged between the outlet opening and the oven and which delimits a contamination-free region in the pressure line, with the outlet opening of the sample line being arranged in the contamination-free region of the pressure line.

The present invention resolves prior art problems by providing a contamination barrier to prevent contamination of the sample fluid emerging from the sample line by contamination fluids occurring in the pressure line. As a result, the precision of the analytical results or the reproducibility of experiments can be increased.

According to another aspect of the present invention, method for treating a sample fluid in a pressure reactor includes conducting the sample fluid in a sample line through an oven to an outlet opening of the sample line into a pressure line in surrounding relation to the sample line, diffusing a contamination fluid through the sample line into the pressure line substantially in a region of the oven, and preventing the contamination fluid from penetrating a contamination-free region in which the outlet opening is arranged by a contamination barrier.

Reference is hereby made expressly to the wording of the claims, as a result of which the claims shall be inserted at this point into the description by reference and shall apply as having been reproduced literally.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
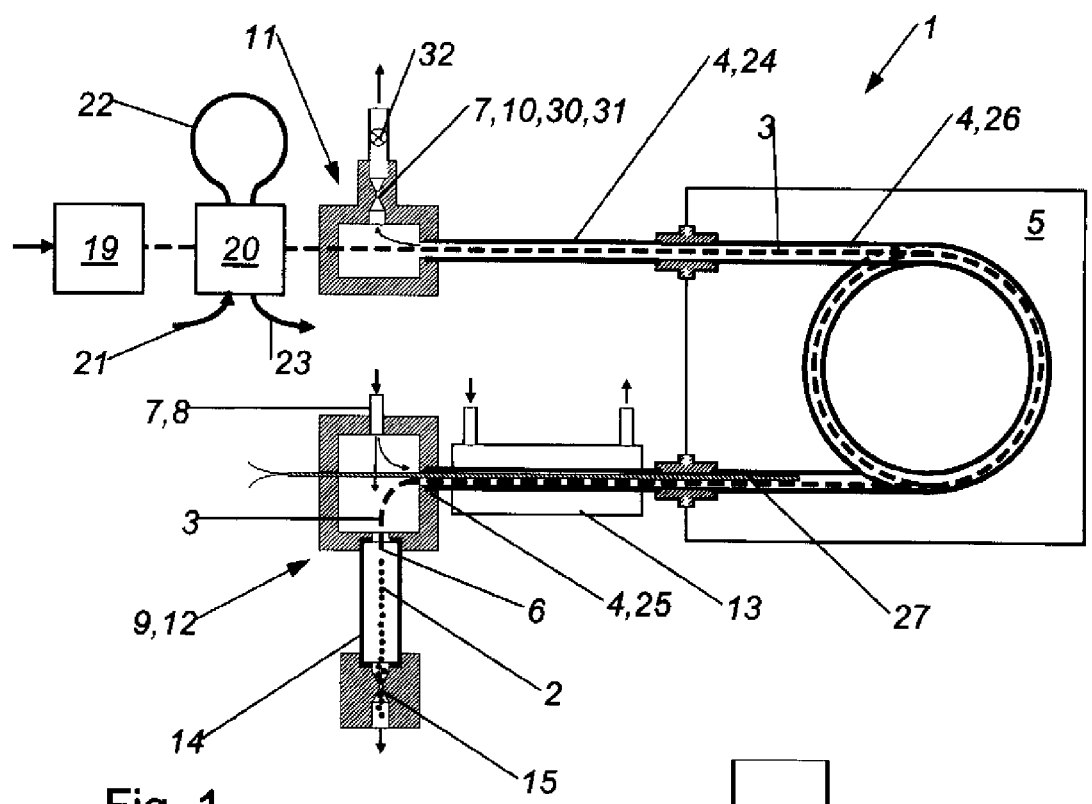
FIG. 1 is a schematic illustration of a first embodiment of a pressure reactor according to the present invention.

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a schematic illustration of a first embodiment of a pressure reactor according to the present invention, generally designated by reference numeral 1 for treating a sample fluid 2. The pressure reactor includes a sample line 3 and a pressure line 4 enclosing the sample line 3, with the sample line 3 and the pressure line 4 partly arranged in an oven 5. The sample line 3 has an outlet opening 6 into the pressure line 4. The sample line 3 can especially be a tube made of PTFE, PFA or a similar material which is substantially chemically inert. Such materials show a high level of chemical resistance on the one hand, but are permeable for diffusion processes on the other hand. Furthermore, the sample line 3 may be configured in one piece and in a homogeneous manner, thereby preventing transitions between different materials which may influence a reaction in an unforeseeable manner.

The sample fluid 2 can be a mixture of a carrier fluid, a sample, especially an organic sample, and at least one reactant, which reactant is to break down the sample and to make the same accessible for further analytic processes. The sample fluid 2 can therefore also be referred to as a reaction mixture. The sample to be broken down can be present in this case as a fluid and/or as a solid body, wherein the sample fluid 2 can also be arranged as a suspension in the case of a solid sample.

The sample line 3, which is surrounded by a pressure line 4, leads through the oven 5, with the outlet opening 6 of the sample line 3 arranged in the pressure line 4, especially outside of the oven 5. The outlet opening 6 may hereby represent a free and open end of the sample line 3. The pressure line 4 is a pressure vessel which encloses the sample line 3, wherein the pressure between the sample line 3 and the pressure line 4 is identical as a result of the outlet opening 6 of the sample line 3 which is arranged in the pressure line 4, by means of which the mechanical loading of the sample line 3 can be kept at a low level. The pressure in the pressure line 4 may hereby range between 10 bars and 60 bars. Advantageously, the pressure in the pressure line 4 is spatially substantially constant, i.e. that substantially the same pressure prevails everywhere in the pressure line 4. It can further be provided that the temperature in the oven is between 100° C. and 270° C.

The pressure line 4 includes a contamination blocking apparatus 7 for forming a contamination barrier arranged at least in sections between the outlet opening 6 and the oven 5. The contamination barrier delimits a contamination-free region 9 in the pressure line 4, with the outlet opening 6 arranged in the contamination-free region 9 of the pressure line 4. A diffusion of various contamination fluids through the sample line 3 may occur in the region of the oven 5 as a result of high temperature. The contamination fluids accumulate hereby in the pressure line 4, especially in the region between the sample line 3 and the pressure line 4, and may subsequently contaminate the finished sample fluid 2 emerging from the outlet opening 6. The contamination blocking apparatus 7 produces a contamination barrier which substantially prevents the contamination fluids from penetrating a contamination-free region 9 around the outlet opening 6. The contamination-free region 9 can especially be substantially free of contamination, i.e. contain slight traces of the contamination fluid, which especially has less than 1%, more preferably less than 1 per mil, of the concentration which would be present without the contamination blocking apparatus 7 in the region around the outlet opening 6. The contamination barrier substantially does not produce any pressure difference, i.e. it is pressure-permeable, by means of which substantially the same pressure will prevail in the region around the outlet opening 6 and in the oven 5. As a result, a contamination fluid can be prevented from contaminating the sample fluid 2 emerging from the outlet opening 6. As a result, the precision of analytical results or the reproducibility of experiments can be increased.

It is provided in the method for treating the sample fluid 2 in the pressure reactor 1 that the sample fluid 2 in the sample line 3 which is surrounded by the pressure line 4 is guided through the oven 5 to the outlet opening 6 of the sample line 3 into the pressure line 4, and that a contamination fluid will diffuse through the sample line 3 into the pressure line 4 substantially in the region of the oven 5. The sample fluid 2 can be heated in the region of the oven 5 in order to produce a chemical reaction for example. As a result of the increased temperature, a diffusion of components of the sample fluid 2 can be produced through the sample line 3 into the surrounding pressure line 4, i.e. into the space between the sample line 3 and a pressure line 4. These components of the sample fluid 2 in the pressure line represent a contamination in this case which can be present in a fluid or gaseous way, as a result of which these diffused components can be regarded as contamination fluid.

This method can be performed continuously or discontinuously. In the continuous method, the sample fluid 2 will be supplied, treated and discharged continuously in the pressure reactor 1. In the discontinuous method, the sample fluid 2 is supplied first to the pressure reactor 1, thereupon treated in a substantially dormant manner, and discharged after the completion of the treatment in its entirety from the pressure reactor 1.

In order to prevent a contamination of the sample fluid 2, which reaches the pressure line 4 through the outlet opening 6, by the contamination fluid which diffuses through the sample line 3 into the pressure line in the region of the oven 5, it is provided that the contamination fluid is prevented by a contamination barrier from penetrating a contamination-free region 9 in which the outlet opening 6 is arranged. As a result, a contamination fluid can be prevented from contaminating the sample fluid 2 which emerges from the outlet opening 6. As a result, the precision of analytical results or the reproducibility of experiments can be increased.

As shown in FIG. 1, the carrier fluid is supplied by a pre-pump 19 to a dosing device 20. The dosing device 20 may have an input 21 for the sample and/or at least one reactant, wherein the reactant can be an acid which is to react with the sample. The dosing device 20 can have a sample loop 22 in which the mixture of carrier fluid, sample and/or reactant is stored until the intended composition of the sample fluid 2 is achieved. Excess carrier fluid or other fluids can be removed in this case from the dosing device 20 especially via an outlet 23.

After reaching the desired composition, the sample fluid 2 is supplied to the sample line 3 which is arranged in the pressure line 4. The sample line 3 is shown in this case as a dashed line in FIG. 1.

The reaction of the individual components of the sample fluid 2 substantially occurs in the oven 5. Advantageously, the oven 5 is a microwave oven and the sample line 3 and the pressure line 4 are microwave-transparent at least in the region of the oven 5. A microwave oven offers the advantage of a constant energy absorption in the sample fluid 2, thereby achieving an even distribution in the temperature and consequently constant reaction speeds. PTFE, and Teflon in particular, or PFA can be provided as microwave-transparent material for the sample line 3. The pressure line 4 may be made of glass or quartz.

Ovens 5 which operate under a different operating principle can alternatively also be used, e.g. an electric resistance heating or a gas heating.

It can further be provided that the sample line 3 and the pressure line 4 are arranged at least partly in a helical way in the region of the oven 5, wherein the pressure line 4 will follow the course of the sample line 3. As a result, the distance of the sample line 3 in the oven 5 can be kept at a high level. In this case, the sample line 3 and the pressure line 4 can include up to 20 windings.

The pressure line 4 has a compressed gas inlet 8 for pressurizing by means of a compressed gas. The compressed gas inlet 8 is arranged in the contamination-free region 9. The compressed gas can be a slow-reacting or in inert gas such as nitrogen or argon. The compressed gas can produce a pressure and a resulting increase in the boiling point of the various components of the sample fluid 2. The arrangement of the compressed gas inlet 8 in the contamination-free region 9 further allows compressed gas to maintain the contamination barrier since the movement or the pressure of the compressed gas will act away from the outlet opening 6 in the direction towards the oven.

The contamination blocking apparatus 7 is constructed as a counter-flow apparatus with compressed gas inlet 8 and compressed gas outlet 10 which advantageously is configured as a flow limiter. The contamination barrier is formed by a flow of the compressed gas from the compressed gas inlet 8 to the compressed gas outlet 10. As a result, the contamination barrier can be produced by a directed flow of the compressed gas, wherein the compressed gas additionally removes the contamination fluids from the pressure reactor through the compressed gas outlet 10. As a result, damage to the pressure line 4 by prolonged action of the contamination fluids can be prevented in this manner.

The contamination fluid outlet 7 is constructed as a flow limiter. A flow limiter can also be designated as a restrictor or throttle and allows the flow of a fluid, wherein a pressure difference between the inner and outer area can be maintained. As a result, a counter-flow apparatus can be arranged in a simple way by the pressure gas inlet 8 and the pressure gas outlet 10 for the flow of a compressed gas in the direction of the oven 5 which is arranged at least in sections between the outlet opening 6 and the oven 5, wherein additional pumps can be avoided.

The contamination barrier may be formed by a flow of a compressed gas from the contamination-free region 9 in the direction of the oven 5. As a result, the sample fluid 2 can be treated in a continuous process because there is a permanent and continuous discharge of the contamination fluid. In this case, the compressed gas flows at least into a region of the pressure line 4, which is arranged between the outlet opening 6 and the contamination fluid outlet 7, from the contamination-free region 9 in the direction towards the compressed gas outlet 10, wherein the compressed gas will entrain the contamination fluid and discharge the same through the pressure gas outlet 10.

As an alternative, the contamination blocking apparatus 7 is arranged for forming a phase boundary between the compressed gas and an absorbing fluid as the contamination barrier, and the contamination-free region 9 is provided for filling with the compressed gas. The phase boundary can hereby be configured as the surface of the absorbing fluid which adjoins the compressed gas. In this case, the phase boundary substantially prevents a transport of the contamination fluid via the phase boundary into the compressed gas in the contamination-free region 9.

For formation of the contamination barrier by means of a phase boundary, the pressure line 4 can be formed in such a way that in the operating position of the pressure reactor 1 at least a part of the pressure line 4 is arranged entirely above the phase boundary at least in the contamination-free region 9, by means of which a flow of the absorbing fluid into the contamination-free region 9 can be prevented during operation. The contamination fluid can thus be kept away from the outlet opening 6 by means of an alternative method described below, wherein the consumption of compressed gas can be kept at a low level. Reference is hereby made to the fact that FIG. 1 only shows a principal diagram and that the pressure line 4 can especially be arranged in such a way that the absorbing fluid can be kept away from the outlet opening 6 and the sample fluid 2 which emerges from the outlet opening 6.

Various fluids can be used as the absorbing fluid, which in turn do not cause any contamination of the sample fluid 2. In particular, distilled water can be used as the contamination absorbing fluid.

A part of the pressure line 4 can substantially be arranged as a siphon for this purpose, which siphon is arranged between the oven 5 and the contamination-free region 9.

Advantageously, the pressure line 4 can be filled with the absorbing fluid at least in the region of the oven 5. As a result, the contamination fluid will be absorbed by the absorbing fluid immediately after diffusion and can easily be removed in this way by means of said fluid.

The entire pressure line 4, with the exception of the contamination-free region 9, may be designed for filling with the absorbing fluid. Since a fluid is substantially incompressible, the phase boundary between the compressed gas and the absorbing fluid remains at a predetermined location in the case of a rise in the pressure by the compressed gas, by means of which the position of the contamination barrier can be predetermined very well.

The pressure line 4 may have an absorbing fluid inlet 31 for filling the pressure line 4 with the absorbing fluid and an absorbing fluid outlet 32 for discharging the absorbing fluid. The absorbing fluid inlet 31 and the absorbing fluid outlet 32 can be closed, especially by a shut-off valve 32, so that no leakage of sample fluid occurs during the treatment of the sample fluid 2. It can especially be provided in this case according to FIG. 1 in a pressure reactor that the compressed gas outlet 10 is arranged as an absorbing fluid inlet 31 and/or absorbing fluid outlet 32, as a result of which both methods can be carried out with a preferred embodiment.

The pressure line 4, especially at least in the region of the oven 5, can be filled with an absorbing fluid, and the contamination-free region 9 can be filled with a compressed gas, with the contamination barrier being formed by a phase boundary between the compressed gas and the fluid. Consequently, compressed gas does not need to escape continuously from the compressed gas outlet 10 in order to remove the contamination fluid. It can be provided in this case that the absorbing fluid can be pressed by the pressure of the compressed gas out of the absorbing fluid outlet 31. Especially in the case of a discontinuous treatment of the sample fluid 2, a consumption of the compressed gas during the treatment can be avoided entirely.

As an alternative, the pressure line 4 can be filled at least in the region of the oven 5 with an absorbing fluid, with the contamination fluid being dissolved in the absorbing fluid, and the contamination fluid dissolved in the absorbing fluid can be discharged through the absorbing fluid outlet 31.

The absorbing fluid is filled into the pressure line 4 in the region of the oven 5 through the absorbing fluid inlet 30. Subsequently the absorbing fluid inlet 30 is closed, especially by the shut-off valve 32, and subsequently the pressure line 4 is subjected to pressure by the compressed gas inlet 8. Then, treatment of the sample fluid 2 is performed, wherein the contamination fluid diffuses through the sample line 3 into the pressure line 4 and is dissolved there in the absorbing fluid and is therefore absorbed. After the treatment of the sample fluid 2, the absorbing fluid outlet 31 and especially the shut-off valve 32 is opened, and the mixture of absorbing fluid and contamination fluid is pressed by the compressed gas out of the absorbing fluid outlet 31.

Although not shown in the drawing, the contamination blocking apparatus 7 may be constructed as a movable gas-tight piston in the pressure line 4 to separate the contamination-free region 9 from the oven. A pressure-permeable contamination barrier can be arranged in this way. The contamination blocking apparatus 7 may also be constructed as a so-called cold trap, in which a gaseous contamination fluid will condense before reaching the contamination-free region 9.

Advantageously, the pressure line 4 is substantially tubular and has a first end 11 and a second end 12. The sample line 3 is introduced into the pressure line 4 in the region of the first end 11, and the outlet opening 6 is arranged in the region of the second end 12. This elongated shape allows providing a flow of the compressed gas in an especially good way, which forms a reliable contamination barrier. Furthermore, the consumption of compressed gas or absorbing fluid can be kept at a low level in this way.

Advantageously, the compressed gas inlet 8 is arranged in the region of the second end 12 and the compressed gas outlet 10 in the region of the first end 11. As a result, the contamination fluid can reliably be cleaned substantially from the entire space within the pressure line 4.

The sample line 4 may have an inside diameter of 1 mm to 4 mm and an outside diameter of 2 mm to 7 mm. The inside diameter of the pressure line 4 in the region of the oven 5 can especially be between 2 mm and 8 mm, wherein the inside diameter of the pressure line 4 is larger than the outside diameter of the sample line 4.

The pressure line 4 may be constructed in several parts. For example, the pressure line 4 has a first section 24 at first end 11, a second section 25 at the second end 12, and a third section 26 arranged between the first section 24 and the second section 25 in the oven 5. In this case, the different sections 24, 25, 26 can be made of different materials. For example, the first section 24 and the second section 25 may advantageously be made of special stainless steel, whereas the third section 26 may be made of glass or quartz.

As further shown in FIG. 1, a cooling system 13 is arranged in a region between the oven 5 and the outlet opening 6. In addition to cooling the sample fluid 2, it is possible to achieve a reliable condensation of the contamination fluid before reaching the outlet opening 6, thus preventing the contamination of the sample fluid 2 at the outlet opening 6 in a better way. This cooling system 13 can be arranged in different ways. A gas or water cooling system can be provided for example according to FIG. 1. An electric cooling system 13, which includes Peltier elements for example, can also be provided. A temperature sensor 27 can be arranged between the sample line 3 and the pressure line 4 and may be constructed as an electric resistance thermometer.

In order to collect the sample fluid 2 emerging from the outlet opening 6 and to convey it from the pressure line 4, the pressure line 4 is designed beneath the outlet opening 6 as a fluid collection container 14 (as seen in the operating position of the pressure reactor 1). The fluid collection container 14 includes a sample fluid output 15. The pressure line 4 can be constructed in a transparent manner in the fluid collection container 14 in order to enable visual checking of the sample fluid 2. The sample fluid output 15 is used for removing the completed sample fluid 2 from the pressure reactor and may be designed as a flow limiter. As a result, the pressure reactor 1 can easily be operated in a continuous process, wherein parts of the compressed gas will flow out of the sample fluid output 15 together with the completed sample fluid 2.

The arrows in FIG. 1 indicate the direction of flow of compressed gas when the pressure reactor 1 operates in a continuous process, wherein the contamination fluid will be removed with the compressed gas. In this case, compressed gas is split into two flows downstream of the compressed gas inlet 8, with a first flow of compressed gas conveying the sample fluid 2 from the sample fluid output 15, whereas the second flow of compressed gas removes the contamination fluid through the compressed gas outlet 10. As a result, the pressure reactor 1 can be easily operated in a continuous process, although accompanied by a resulting high consumption of compressed gas.

Although not shown in the drawing, the pressure reactor 1 may also be operated in a discontinuous manner, with a valve being arranged in the sample fluid output 15. In this case, the valve is closed during treatment of the sample fluid 2. After the treatment of the sample fluid 2, the valve in the sample fluid output 15 is opened and the sample fluid 2 is discharged. This prevents a loss of compressed gas during the discontinuous process, but only in the case of a discontinuous process.

Figure 2:
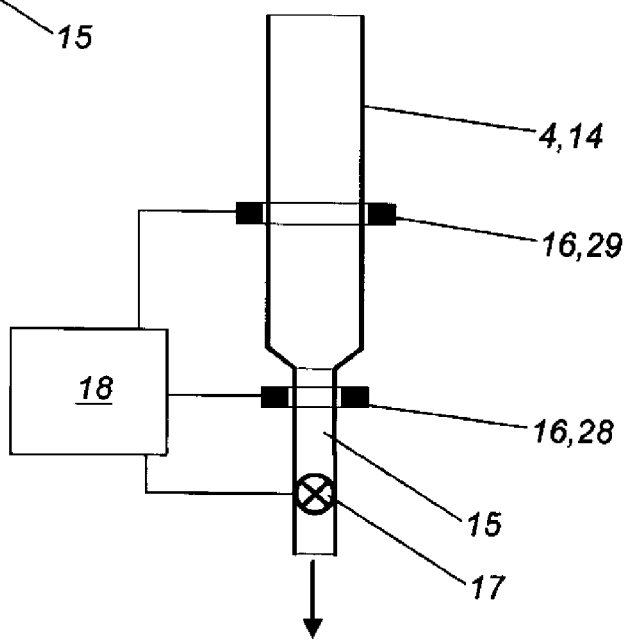
FIG. 2 is a schematic detailed cutaway view of a second embodiment of a pressure reactor according to the present invention.

FIG. 2 shows the region of the sample fluid output 15 of a second embodiment of the pressure reactor 1. Parts corresponding with those in FIG. 1 are denoted by identical reference numerals and not explained again. The description below will center on the differences between the embodiments. In this embodiment, provision is made for a filling-level meter 16 which is arranged in the fluid collection container 14. The filling-level meter 16 is operably connected to the input of a control device 18 which controls the discharge of the sample fluid 2 through the sample fluid output 15 by means of a valve 17. As a result, the sample fluid can also be removed continuously in a continuous process, wherein a loss of compressed gas through the sample fluid output 15 can substantially be avoided.

Advantageously, a minimum filling level of the sample fluid 2 is predetermined in the fluid collection container 14 of the pressure line 4 which contains the sample fluid output 15, which fluid collection container 14 is arranged beneath the outlet opening 6 as seen in the operating position of the pressure reactor 1. A filling level is determined in the fluid collection container 14, and the sample fluid 2 is discharged through the sample fluid output 15 from the pressure line 4 (especially automatically controllable by a control device 18) only when the filling level is higher than the minimum filling level. The minimum filling level can prevent the escape of the pressure gas through the sample fluid output 15. As a result, the sample fluid can also be taken continuously in the case of a continuous process.

The filling-level meter 16 can operate in various manners known to the person skilled in the art.

Only the reaching of specific filling levels can be measured for example, e.g. via the electric resistance or via capacitive sensors 28, 29.

The sample fluid 2 is discharged from the pressure line 4 through the sample fluid output 15 in the fluid collection container 14 until the predeterminable minimum filling level of the sample fluid 2 is reached. Upon reaching the minimum filling level, the sample fluid output 15 is closed off, especially by the valve 17, and the sample fluid output 15 is opened when a predeterminable maximum filling level is reached. The filling-level meter 16 can be designed in an especially simple way in this method.

The filling-level meter 16 has a bottom capacitive sensor 28 and an upper capacitive sensor 29. Both capacitive sensors 28, 29 are operably connected to the control device 18. The bottom passive sensor 28 determines the minimum filling level. When the filling level drops towards the bottom capacitive sensor 28, the valve 17 is closed by the control device 18. Once the valve 17 has been closed, the filling level 2 will rise in the fluid collection container 14 until the upper passive sensor 29 is reached. The upper capacitive sensor 29 determines the predeterminable maximum filling level. The valve 17 is then opened by the control device 18 until the filling level drops again to the bottom capacitive sensor 28. As a result, the filling-level meter 16 can be designed in an especially simple and reliable way.

As an alternative, a minimum filling level is predetermined, and the sample fluid output 15 is closed when the minimum filling level is reached. After a predeterminable time interval after the closing of the sample fluid output 15, the sample fluid output 15 is cleared again, especially by the control device 18. The predeterminable time interval can especially be stored in the control device 18. Advantageously, the predeterminable time interval can be selected depending on the conveying capacity of the pre-pump 19. The pressure reactor 1 can thus be designed in an especially simple and reliable way.

The filling-level meter 16 may also be configured for determining the current filling level, with the valve 17 being designed as a controllable throttle valve with controllable guide value. It can be provided for example that the filling-level meter 16 operates by means of a float or a visual process, wherein the current filling level can be determined. A target filling level may hereby be predefined, which target filling level lies above the minimum filling level. A current filling level is determined. A deviation between the target filling level and the current filling level is used as an actuating quantity of a control loop. As a function of the actuating quantity, a valve in the sample fluid outlet 15 is controlled in such a way that the current filling level corresponds to the target filling level. This has the advantage that in the case of a continuous process, especially when the sample fluid 2 flows with substantially constant speed into the fluid collection container 14, the sample fluid 2 exits the pressure rector at substantially constant speed. As a result, fluctuations in the pressure caused by opening and closing of the valve 17 can be kept to a minimum.

The amount of sample fluid 2 for the maximum filling level may be at least twice the amount of sample fluid 2 for the minimum filling level.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. A pressure reactor for treating a sample fluid, said pressure reactor comprising:
   an oven;
   a sample line partly arranged in the oven;
   a pressure line surrounding the sample line and partly arranged in the oven, said sample line having an outlet opening into the pressure line; and
   a contamination blocking apparatus disposed in the pressure line for forming a contamination barrier which has at least one section arranged between the outlet opening and the oven and which delimits a contamination-free region in the pressure line, said outlet opening of the sample line being arranged in the contamination-free region of the pressure line.

2. The pressure reactor of claim 1, wherein the pressure line has a compressed gas inlet for pressurization by a compressed gas, said compressed gas inlet being arranged in the contamination-free region.

3. The pressure reactor of claim 2, wherein the contamination blocking apparatus is arranged as a counter-flow apparatus with the compressed gas inlet and a compressed gas outlet, said contamination barrier being formed by a flow of compressed gas from the compressed gas inlet to the compressed gas outlet.

4. The pressure reactor of claim 3, wherein the compressed gas outlet is configured as a flow limiter.

5. The pressure reactor of claim 2, wherein the contamination blocking apparatus is configured for forming a phase boundary between the compressed gas and an absorption fluid as a contamination barrier, said contamination-free region being configured for filling with the compressed gas.

6. The pressure reactor of claim 5, wherein the pressure line is configured to receive the absorption fluid at least in a region of the oven.

7. The pressure reactor of claim 1, wherein the oven is a microwave oven, said sample line and said pressure line being microwave-transparent at least in a region of the oven.

8. The pressure reactor of claim 1, wherein the pressure line is substantially tubular and has first and second ends, said sample line being introduced into the pressure line in a region of the first end, with the outlet opening of the sample line arranged in a region of the second end.

9. The pressure reactor of claim 1, further comprising a cooling system arranged in a region between the oven and the outlet opening.

10. The pressure reactor of claim 1, wherein the pressure line is arranged beneath the outlet opening to form a fluid collection container, when the pressure reactor is operational, said fluid collection container having a sample fluid output configured as a flow limiter.

11. The pressure reactor of claim 1, wherein the pressure line is arranged beneath the outlet opening to form a fluid collection container, when the pressure reactor is operational, said fluid collection container having a sample fluid output, and further comprising a filling-level meter arranged in the fluid collection container and operably connected to an input of a control device for controlling a discharge of the sample fluid through the sample fluid output via a valve.

\* \* \* \* \*